USO05762616A

United States Patent [19]

Talish

[11] Patent Number: 5,762,616
[45] Date of Patent: Jun. 9, 1998

[54] APPARATUS FOR ULTRASONIC TREATMENT OF SITES CORRESPONDING TO THE TORSO

[75] Inventor: Roger J. Talish, Fairfield, N.J.

[73] Assignee: Exogen, Inc., Piscataway, N.J.

[21] Appl. No.: 618,462

[22] Filed: Mar. 15, 1996

[51] Int. Cl.$^6$ .................................................. A61B 17/56
[52] U.S. Cl. .................................................................. 601/2
[58] Field of Search ........................... 601/2; 600/9, 15; 128/660.03

[56] References Cited

U.S. PATENT DOCUMENTS

| | | |
|---|---|---|
| 2,799,787 | 7/1957 | Güttner et al. |
| 3,499,437 | 3/1970 | Balamuth |
| 4,175,565 | 11/1979 | Chiarenza et al. |
| 4,530,360 | 7/1985 | Duarte |
| 4,556,066 | 12/1985 | Semrow |
| 4,708,127 | 11/1987 | Abdelghani |
| 4,787,070 | 11/1988 | Suzuki et al. |
| 4,798,539 | 1/1989 | Henry et al. |
| 4,867,169 | 9/1989 | Machida et al. |
| 4,936,303 | 6/1990 | Detweiler et al. |
| 5,003,965 | 4/1991 | Talish et al. |
| 5,072,724 | 12/1991 | Marcus |
| 5,134,999 | 8/1992 | Osipov |
| 5,186,162 | 2/1993 | Talish et al. |
| 5,211,160 | 5/1993 | Talish et al. |
| 5,259,384 | 11/1993 | Kaufman et al. |
| 5,309,898 | 5/1994 | Kaufman et al. |
| 5,314,401 | 5/1994 | Tepper |
| 5,327,890 | 7/1994 | Matura et al. |
| 5,351,389 | 10/1994 | Erickson et al. .................... 600/9 |
| 5,378,225 | 1/1995 | Chatman, Jr. et al. |
| 5,415,167 | 5/1995 | Wilk |
| 5,556,372 | 9/1996 | Talish et al. ........................... 601/2 |

FOREIGN PATENT DOCUMENTS

| | | |
|---|---|---|
| 47358 | 3/1987 | Japan |
| 47359 | 3/1987 | Japan |
| 82567 | 3/1992 | Japan |
| 82568 | 3/1992 | Japan |
| 82569 | 3/1992 | Japan |
| 269159 | 10/1993 | Japan |
| 8800845 | 2/1988 | WIPO |

OTHER PUBLICATIONS

1975 Abstract (Proceedings of the III Congress on Biomedical Engineering), "Ultrasonic Action on Callus Formation in Bones".

1976 Abstract (Proceedings of the 11th International Conference on Medical and Biological Engineering), "Ultrasonic Stimulation of Fracture Healing".

1977 Abstract (Proceedings of the IV Brazilian Congress on Biomedical Engineering), "Ultrasound in the Treatment of Fractures".

T. Arai et al., "The Effect of Ultrasound Stimulation On Disuse Osteoporosis", Thirteenth Annual Meeting of BRAGS Dana Point, CA, 1993.

L. R. Duarte, "The Stimulation of Bone Growth by Ultrasound", Arch. Orthop. Trauma Surg., 1983, 101, pp. 153–159.

C. A. M. Xavier et al., RTD–65–4 "A Non-Invasive Form of Ultrasound Stimulation of Ununited Fractures", Sep. 1981.

Primary Examiner—Marvin M. Lateef
Assistant Examiner—Derrick Fields
Attorney, Agent, or Firm—Dilworth & Barrese

[57] ABSTRACT

The apparatus is used for therapeutically treating injuries using ultrasound. The apparatus includes an ergonomically constructed ultrasonic transducer treatment head module and a portable, ergonomically constructed main operating unit. The transducer treatment head module is positioned adjacent the area of the injury and excited for a predetermined period of time. The apparatus includes means for positioning and holding the treatment head module adjacent positions on the torso of the body, such as the clavicle, the pelvis, the hip and the spine.

31 Claims, 12 Drawing Sheets

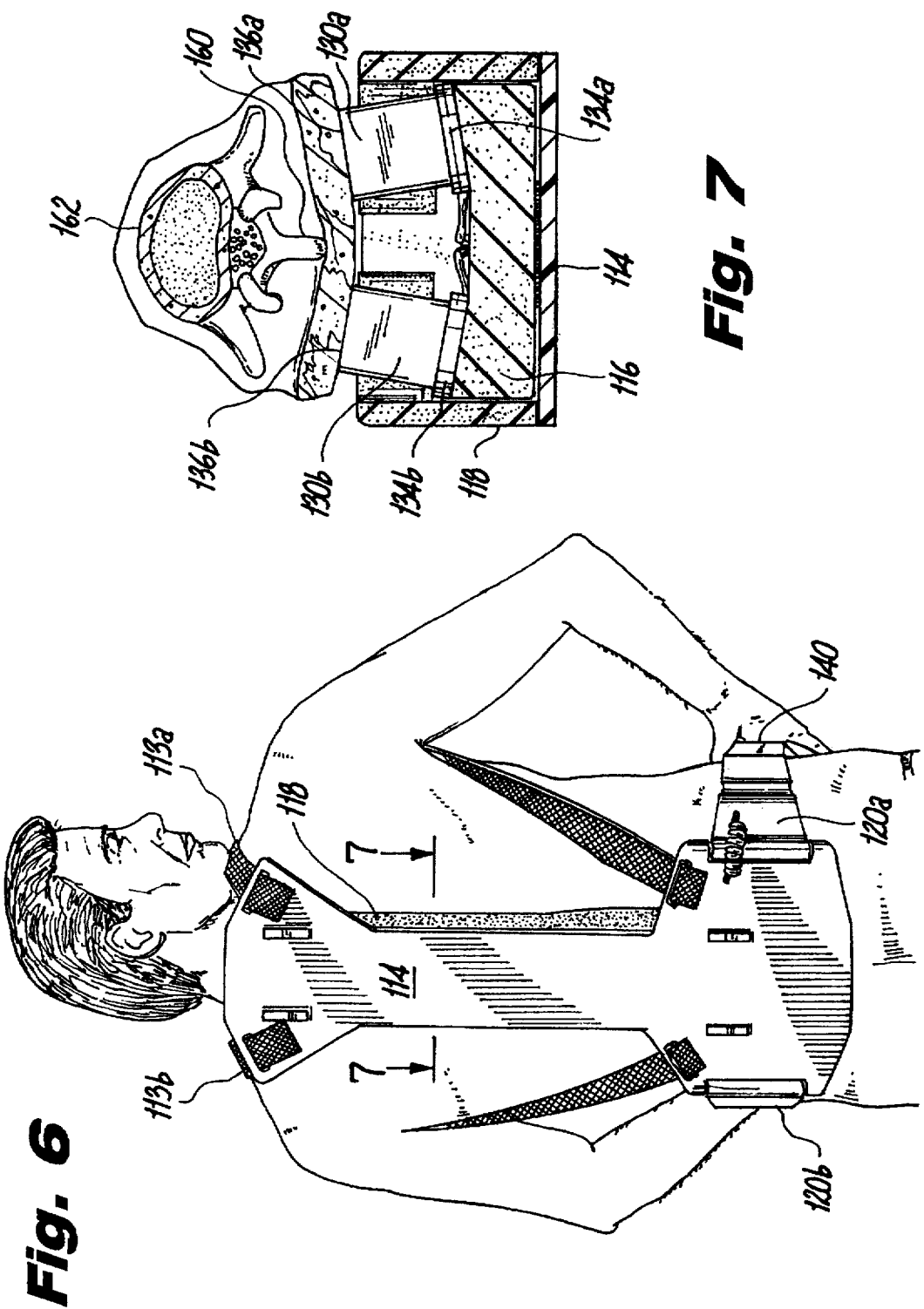

APPARATUS FOR ULTRASONIC TREATMENT OF SITES CORRESPONDING TO THE TORSO

BACKGROUND OF THE INVENTION

1. Field of the Invention

The present invention relates to an apparatus for therapeutically treating bone structure using ultrasound. More particularly, the present invention relates to an apparatus which utilizes a portable ergonomically constructed signal generator, an ergonomically constructed transducer and attachment apparatus for treating bone injuries or a variety of musculoskeletal injuries and/or problems.

2. Description of the Related Art

The use of ultrasound to therapeutically treat and evaluate bone injuries is known. Impinging ultrasonic pulses having appropriate parameters, e.g., frequency, pulse repetition, and amplitude, for suitable periods of time and at a proper external location adjacent to a bone injury has been determined to accelerate the natural healing of, for example, bone breaks and fractures. For patients with reduced healing capacity, such as elderly persons with osteoporosis, ultrasonic therapy may promote healing of bone injuries that would otherwise require prosthetic replacement or leave the patient permanently disabled.

U.S. Pat. No. 4,530,360 to Duarte describes a basic non-invasive therapeutic technique and apparatus for applying ultrasonic pulses from an operative surface placed on the skin at a location adjacent a bone injury. The applicator described in the '360 patent has a plastic tube which serves as a grip for the operator, an RF plug attached to the plastic tube for connection to an RF source, and internal cabling connected to an ultrasonic transducer. To apply the ultrasound pulses during treatment an operator must manually hold the applicator in place until the treatment is complete. As a result, the patient is, in effect, immobilized during treatment. The longer the treatment period, the more the patient and/or the assistant is inconvenienced, and certain parts of the body, such as the back, cannot be reached by the patient with such a device, thus requiring the help of an assistant. The '360 patent also describes a range of RF signals for creating the ultrasound, ultrasound power density levels, a range of duration for each ultrasonic pulse, and a range of ultrasonic pulse frequencies.

U.S. Pat. No. 5,003,965 to Talish et al. relates to an ultrasonic body treatment system having a body-applicator unit connected to a remote control unit by sheathed fiber optic lines. The signals controlling the duration of ultrasonic pulses and the pulse repetition frequency are generated apart from the body-applicator unit. Talish et al. also describes a mounting fixture that is adapted for use with a cast for attaching the body-applicator unit to a patient so that the operative surface is adjacent the skin location.

U.S. Pat. No. 5,211,160 to Talish et al. relates to an ultrasonic treatment system with a mounting fixture that attaches to a patient's limb using straps and a hook and loop attachment. The body application unit interfaces with the mounting fixture so that the operative surface is adjacent the skin location.

While the systems described in these patents relate to therapeutic methods and apparatus for ultrasonically treating injured bone, and describe basic mounting fixtures for use with a cast or limb for attaching the body applicator unit to the patient, they do not disclose ergonomically configured signal generators and transducers, and attachments therefor, which permit placement of the body-applicator unit adjacent various parts of the body that are either hard-to-reach or, because of the topology of the external skin location, make it difficult to manually position and maintain a transducer adjacent thereto. Nor do these systems permit patient mobility during treatment.

Therefore, a need exists for apparatus which optimize healing while maintaining patient mobility. In particular, a need exists for an apparatus which permits placement of the body-applicator unit adjacent various parts of the body that are hard-to-reach or otherwise hard to manually position a transducer adjacent thereto, such as the spine, hip, pelvis or clavicle region.

SUMMARY OF THE INVENTION

The ultrasonic treatment apparatus of the present invention is used for therapeutically treating injuries using ultrasound. The apparatus includes a main operating unit, including a signal generator for providing excitation signals for an ultrasonic transducer head module. At least one ultrasonic treatment head module is also provided including a receiving component and an ultrasonic generation component for providing ultrasonic waves from an exposed operative surface positionable adjacent a skin location. The receiving component receives the excitation signals from the signal generator and provides input signals to the ultrasonic generation component for the generation of ultrasonic waves at the operative surface. An interface between the main operating unit and the receiving component of the ultrasonic treatment head module transmits the excitation signals from the signal generator to the receiving component. An attachment, configured to contour at least in part to a region of the torso of a human body includes receptacle means adapted for holding at least one ultrasonic treatment head module with the operative surface adjacent a skin location in the torso region when the attachment is positioned adjacent the torso region it is contoured to.

The invention also includes an ultrasonic delivery system for therapeutic use having at least one ultrasonic treatment module with a telescoping portion. The distal end of the telescoping portion defines a forward planar region. Ultrasonic generation means housed within the at least one ultrasonic treatment module includes an exposed operative surface substantially parallel to the forward planar region of the telescoping portion. A positionable receptacle is provided for retaining and aligning the ultrasonic treatment module with the operative surface adjacent a skin location on a region on the torso of a human body.

The apparatus of the present invention encompasses a variety of specific configurations adapted for treatment on various regions of the torso that are prone to injury, such as the clavicle region, the hip, the pelvis and the spine. (For the purposes of this application, the torso includes the femur. Also, the spine is defined to extend from the cervical vertebrae to the coccyx.) Various embodiments may be worn by the user, thereby allowing patient mobility during use. Also, the various embodiments provide for adjusting the position of the operative surface of the ultrasonic treatment module so that it interfaces with the external skin location on the torso corresponding to the injury targeted for treatment.

BRIEF DESCRIPTION OF THE DRAWINGS

Preferred embodiments of the invention are described below with reference to the drawings, which are described as follows:

FIG. 6 is a rear view of the system of FIGS. 4 and 5 attached for treatment of the lower back and spine of a user;

FIG. 7 is a cross-sectional view of components of the device and body of the patient shown in FIG. 6, taken along lines 6—6;

DETAILED DESCRIPTION OF THE PREFERRED EMBODIMENTS

The ultrasonic treatment apparatus of the present invention is used for therapeutically treating injuries using ultrasound. Although shown here for the treatment of musculoskeletal injuries, other injuries including venous ulcers are also contemplated. The apparatus includes an ergonomically constructed ultrasonic transducer assembly partially fabricated with a conductive plastic material. The apparatus also utilizes a portable, ergonomically constructed main operating unit (MOU) which provides control signals for the ultrasonic transducer treatment head module. The portable MOU may be constructed to fit within a pouch worn by the patient or otherwise attached to the apparatus for portability. In operation, the transducer treatment head module is positioned adjacent the injured area and excited for a predetermined period of time. To ensure that the transducer treatment head module is properly positioned, a safety interlock is provided to prevent inadvertent excitation of the transducer assembly and to insure patient compliance.

The MOU and ultrasonic treatment head module, including the electronics and components of the device, are further described in commonly owned U.S. patent application Ser. Nos. 08/389,148 and 08/367,471, which are incorporated by reference into this application. Also, a gel containment structure to couple the transducer surface with the external skin location is described in commonly-owned U.S. patent application Ser. No. 08/391,109, which is also incorporated by reference into this application.

Although the above-referenced applications show a single transducer treatment head module, the present invention also envisions a plurality of modules for use with a single MOU. (Construction of an MOU to house the electronics necessary to service a plurality of ultrasonic head treatment modules would be a routine task for one skilled in the art using the descriptions for a single module in the above-referenced applications.) The plurality of modules, for example, may all be activated at once.

Many musculoskeletal injuries on the torso occur in places where it is difficult to position and/or maintain the treatment head module. FIGS. 1–16 illustrate apparatus for positioning the transducer treatment head module adjacent difficult locations on the torso, and are described below.

Spine and Back Treatment Apparatus

Figure 1:
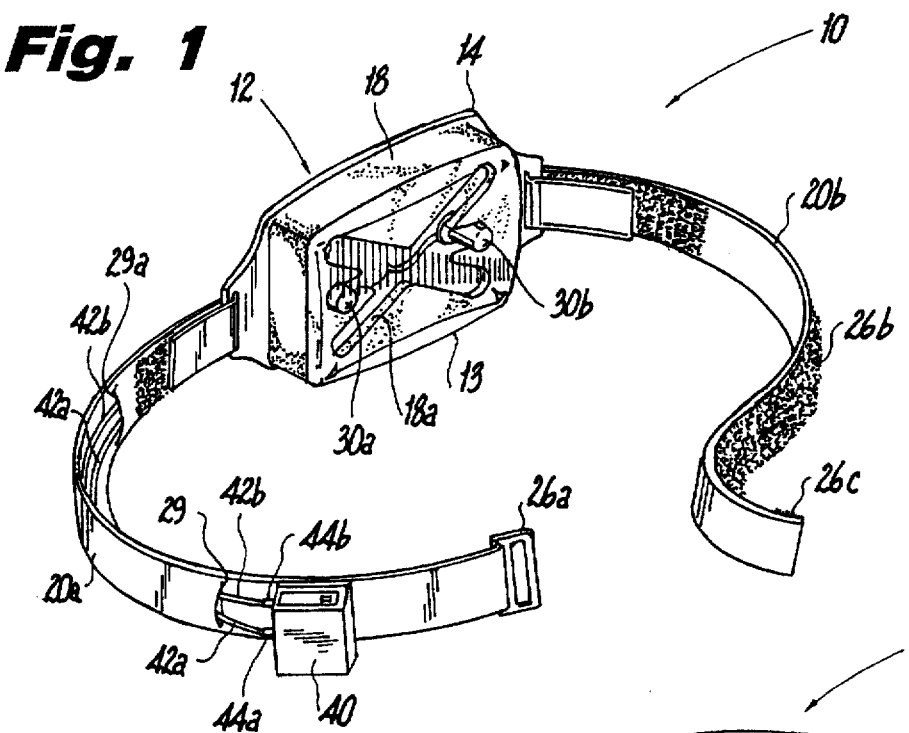
FIG. 1 is a perspective view of a portable module type ultrasonic delivery system configured for use in spinal and back injuries.

FIGS. 1–8 show preferred embodiments of apparatus for delivering ultrasonic therapeutic treatment to the spine and lower back, a region of the torso where it is difficult to position and maintain an ultrasonic treatment module. FIG. 1 is a perspective view of a first preferred embodiment of a spinal treatment apparatus 10, which includes a treatment head module housing portion 12 attached to two belt portions 20a, 20b. Two treatment head modules 30a, 30b are shown extending from the housing portion 12. An ultrasonic conducting wedge 13 is shown attached at the front of the housing portion 12, which is further described below. (For ease of reference, the side of the housing portion 12 from which modules 30a, 30b protrude and on which the ultrasonic conducting wedge 13 is attached is referred to as the "front" of the housing portion, and its constituent components, described below.) A main operating unit ("MOU") 40 is shown attached to belt portion 20a, and cables 42a, 42b extend from MOU 40 along belt portion 20a and through housing portion 12 (in a manner described further below) to treatment head modules 30a, 30b, respectively.

Figure 2:
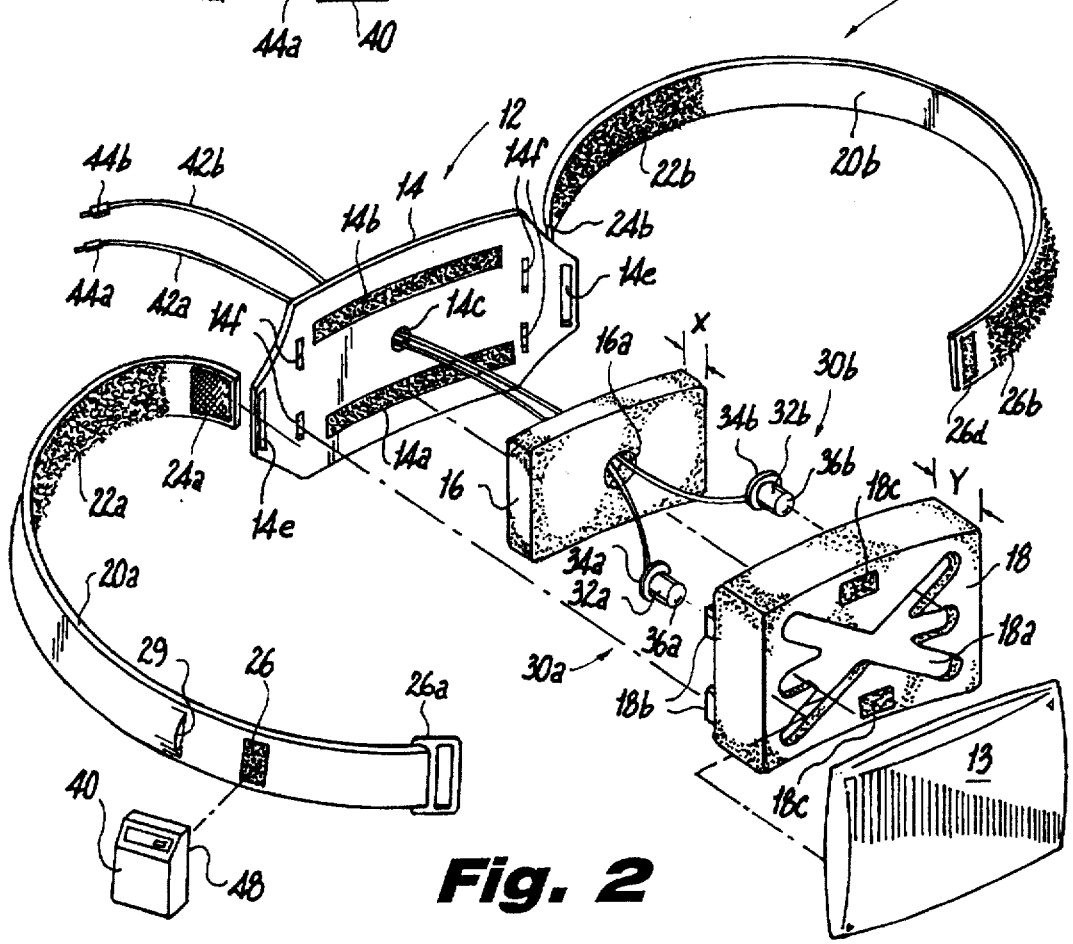
FIG. 2 is an exploded view of the system of FIG. 1.

FIG. 2 is an exploded view of the spinal treatment apparatus of FIG. 1. Housing portion 12 is comprised of a cover 14, enclosure 16, and shell 18. Cover 14 has an oblong octagonal shape, with tabbed portions 14d, 14e for affixing belt portions 20a, 20b, respectively, to the housing portion 12. Cover 14 has a concave curvature when viewed from the front. Cover 14 may be made of partially flexible plastic. Cables 42a, 42b pass through hole 14c in the center of cover 14. Strips of hook fasteners 14a, 14b on cover 14 correspond with matching strips of loop fasteners (not visible in FIG. 2) on the rear of enclosure 16, and position cover 14 with respect to enclosure 16 when the housing portion 12 is assembled.

Enclosure 16 is substantially rectangularly shaped, and cables 42a, 42b pass through hole 16a in the center of enclosure 16. Enclosure 16 is made of a resilient, deformable material, such as foam rubber.

Figure 3:
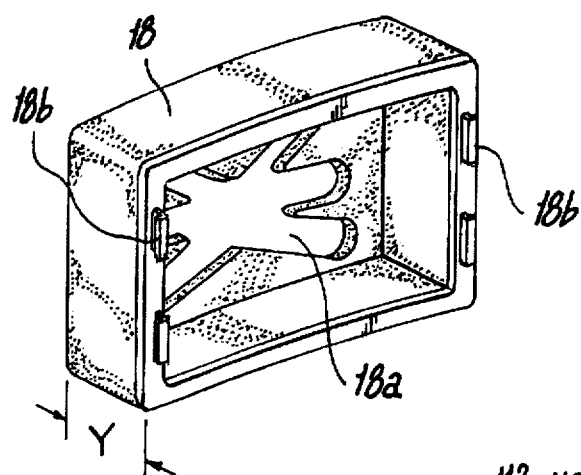
FIG. 3 is a perspective view of one of the components of the system of FIG. 2, viewed from the opposite direction of FIG. 2.

Shell 1a also is rectangularly shaped and may be a flexible, resilient plastic. Shell 18 has a concave curvature when viewed from the front. Module track 18a extends through the front surface of shell 18. As seen in FIG. 3, a rear view of shell 18, shell 18 is substantially hollow, so that enclosure 16 may be received therein. The width of enclosure 16 (labelled "X" in FIG. 2) is greater than the width of shell 18 (labelled "Y" in FIGS. 2 and 3), so that enclosure 16 is compressed when housing 12 is assembled, as further described below.

Referring again to FIG. 2, treatment head modules 30a, 30b have a different profile than those in U.S. patent application Ser. No. 08/389,148, incorporated by reference above, although they will generally house the same electronic circuitry. As seen, treatment head modules 30a, 30b each have a single projecting portion 32a, 32b and a flange portion 34a, 34b adjacent one end of projecting portion 32a, 32b. The flange portions 34a, 34b are opposite the transducer surface 36a, 36b. Cables 42a, 42b extend into the treatment head modules 30a, 30b, respectively, through the rim of flange portions 34a, 34b.

Treatment head modules 30a, 30b may be received in the hollow portion of shell 18, and the projecting portions 32a32b extend through the module track 18a of the shell 18 so that the transducers 36a, 36b protrude from the front of the shell 18 through module track 18a and press against the back side of ultrasonic conducting wedge 13. (This is shown in the FIG. 1, where the housing portion 12 is shown assembled.) Flange portions 34a, 34b abut the back of the front surface of the shell 18, so the head modules 30a, 30b do not pass through the module track 18a completely.

Referring to FIGS. 1 and 2 together, enclosure 16 is received within the shell 18 and the cover 14 and shell are joined together by snap fasteners, such, as the series of ridged tabs 18b on shell 18 that interface with the series of slots 14f on cover 14. The enclosure 16 is compressed when housing portion 12 is assembled, because its width is greater than width of shell 18. Consequently, enclosure 16 will press the flange portions 34a, 34b of the head modules 30a, 30b against the back of the front surface of the shell 18, thereby providing a frictional engagement between the enclosure 16, the flange portion 30a, 30b and the shell 18. This holds the head modules 30a, 30b in a desired position on the module track 18a, with the transducers 36a, 36b protruding from the front of the shell 18.

Belt segments 20a, 20b are used to fasten the housing portion 12 against the spine and lower back. Belt segments 20a, 20b are removably attached to the cover 14 of housing portion 12 by passing hook fastener segments 24a, 24b located on one end of each respective belt segment 20a, 20b through slots 14d, 14e, respectively, of cover 14. Fastening occurs when the end of each belt segment 20a, 20b is looped back on itself around the slot 14d, 14e, respectively, so that hook fastener segment 24a, 24b engages adjacent loop fastener segment 22a, 22b, respectively. (FIG. 1 shows belt segments 20a, 20b attached to the cover 14 in this manner.) Cables 42a, 42b extend from head modules 30a, 30b, respectively, through hole 16a in enclosure 16 and hole 14c in cover 14, as shown in FIG. 2. As seen in FIG. 1, cables 42a, 42b snake through passageways 29, 29a in belt segment 20a, to the MOU 40. Plugs 44a, 44b, attach cables 42a, 42b, respectively, to MOU 40.

Belt segments 20a, 20b attach to each other around the waist of a user by threading an end of belt segment 20b containing adjacent hook and loop fastener segments 26b, 26c, through the buckle 26a of belt segment 20a. The end of the belt segment 20b is looped back on itself around the buckle 26a so that the hook and loop fastener segments 26b, 26c engage. MOU 40 is held near the buckle 26a of belt segment 20a by hook and loop fastener segments 28, 46.

When the belt 20a, 20b is attached about the patient's waist, the spinal treatment apparatus 10 of FIGS. 1-3 is designed to treat both the spine and a region of the back adjacent the spine. The width of the housing portion 12 and the concave curvature of the front surface of the shell 18 allows the front of the shell 18 to engage a wide region of the lower back and spine. The profile of the module track 18a allows transducer surfaces 23a, 23b to be positioned adjacent a broad region of the lower back. (Although two treatment head modules are shown in the figures, one or more than two may be accommodated by the module track 18a.) MOU 40 is conveniently located on the user's waist, at the front of his body, adjacent the belt buckle 26a.

Ultrasonic conducting wedge 13 attaches to the front of shell 18 and provides an acoustically coupling interface between the transducer surfaces 36a, 36b and the external skin location of the patient. (Without such an ultrasonic conducting wedge, conducting gel, or like conducting material, much of the acoustic energy emitted by the transducer is scattered at the discontinuities between the transducer surfaces 36a, 36b and the skin.) The ultrasonic conducting wedge 13 may be an ATS Acoustic Standoff, commercially available from ATS Laboratories, Inc., Bridgeport, Conn. Alternatively, an acoustically coupling interface may be achieved by spreading conducting gel on the transducer surfaces 36a, 36b, or by attaching a gel containment structure (as described in U.S. patent application Ser. No. 08/391,109, incorporated by reference above) to the transducer surfaces 36a, 36b.

It should be noted that the design of the spinal treatment apparatus 10 of FIGS. 1 and 2 allow the use of multiple head modules, positioned as required for treatment within the module track 18a. Also, the apparatus 10 may be easily disassembled for cleaning. It also allows for rapid reconfiguration of the treatment head modules within the module track 18a and/or rapid insertion or withdrawal of treatment head modules.

A second preferred embodiment of a spinal treatment apparatus 110 shown in FIGS. 4-8 focuses the ultrasonic treatment along the spine. Structurally, the apparatus 110 of FIGS. 4-8 is similar to the apparatus 10 of FIGS. 1-3, with the treatment head modules positionable vertically in the apparatus 110, which corresponds to the spine when the apparatus 110 is worn by the user.

Figure 4:
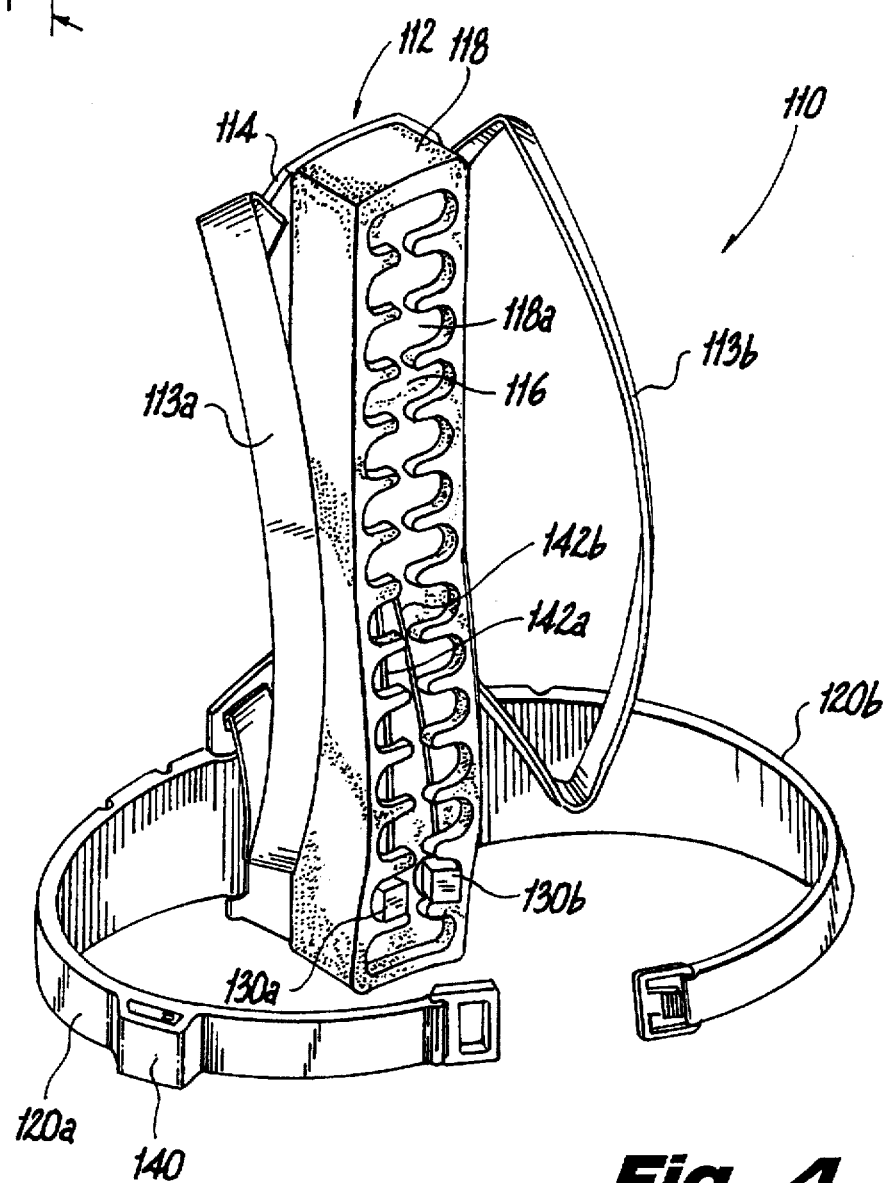
FIG. 4 is a perspective view of a portable module type ultrasonic delivery system configured for use in spinal injuries.

The following description regarding the apparatus 110 shown in FIGS. 4-8 is analogous to the description regarding the apparatus 10 of FIGS. 1-3 above:

FIG. 4 is a perspective view of the spinal treatment apparatus 110, which includes a treatment head module housing portion 112, integral belt portions 120a, 120b, and shoulder straps 113a, 113b. Two treatment head modules 130a, 130b are shown partially extending from the housing portion 112. (For ease of reference, the side of the housing portion 112 from which modules 130a, 130b protrude is again referred to as the "front" of the housing portion 112, and its constituent components, described below. The direction "up" is with respect to the orientation of the apparatus 110 in the drawings.) An MOU 140 is integrally attached to belt portion 120a, and MOU 140 interfaces with head modules 130a, 130b, respectively, via electrical cables 142a, 142b, which extend through housing portion 112 and belt portion 120a in a manner described further below.

Figure 5:
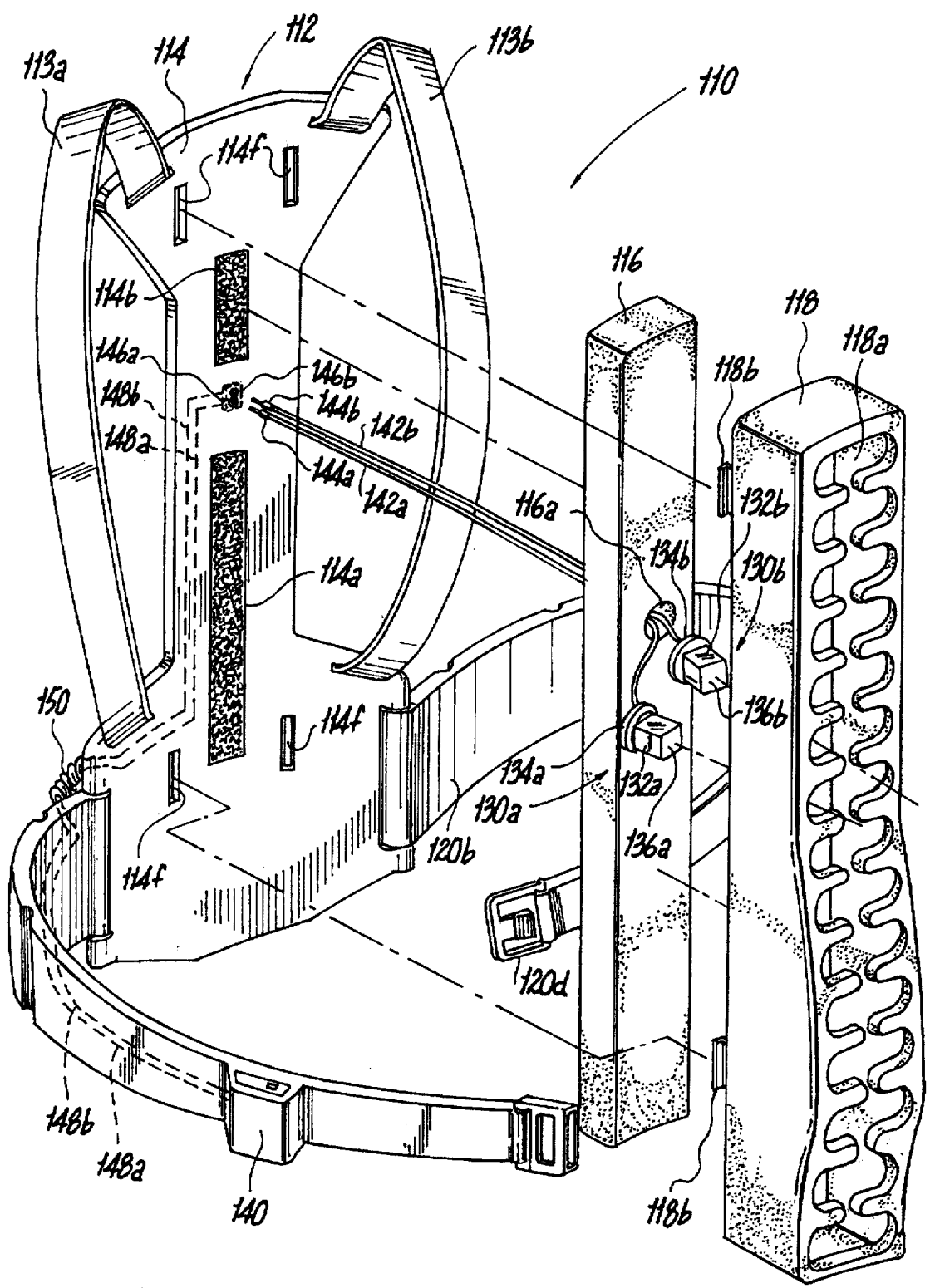
FIG. 5 is an exploded view of the system of FIG. 4.

FIG. 5 is an exploded view of the spinal treatment apparatus 110 of FIG. 4. FIG. 6 is a rear view of the apparatus 110 positioned for treatment on the back of a patient. Referring to FIG. 5, housing portion 112 is comprised of a cover 114, enclosure 116, and shell 118. Cover 114 is oblong in the central region and approximately rectangular at its base. Belt portions 120a, 120b are pivotably attached to cover 114 by a pin (not visible in FIG. 5) that extends through each belt portion 120a, 120b and engages cover 114. Cover 114 may be made of partially flexible, resilient plastic. Jacks 146a, 146b located at the midsection of cover 114 receive plugs 144a, 144b of cables 142a, 142b, as described below. Strips of hook fasteners 114a, 114b on cover 114 correspond with matching strips of loop fasteners (not visible in FIG. 5) on the rear of enclosure 116, and position cover 114 with respect to enclosure 116 when the housing portion 112 is assembled.

Enclosure 116 has an oblong rectangular shape that corresponds to the vertical extension of cover 114. Hole 116a in enclosure 116 is provided for cables 142a, 142b, as described below. Enclosure 116 is made of a resilient, deformable material, such as foam rubber.

Shell 118 also has an oblong rectangular shape that corresponds to the vertical extension of cover 114. Shell 118 may be a partially flexible plastic. Module track 118a extends through and along the length of the front surface of shell 118. Shell 118 is substantially hollow, as is shell 18 shown FIG. 3, so that enclosure 116 may be received therein. The front of shell 118 bulges outward below the midsection in order to contour to the lumbar region, and then recesses in order to cover the coccyx region.

Treatment head modules 130a, 130b are configured as described with respect to FIG. 2, above. That is, treatment head modules 130a, 130b each have a single projecting portion 132a, 132b and a flange portion 134a, 134b adjacent one end of projecting portion 132a, 132b. The flange portion 134a, 134b is opposite the transducer surface 136a, 136b. The transducer surface 136a, 136b of each module 130a, 130b (as well as the projecting portions 132a, 132b) in this embodiment is depicted as rectangularly shaped, however. In general, the profile of the transducer surfaces for any embodiment may be tailored for the particular therapeutic treatment. Cables 142a, 142b extend into the treatment head modules 130a, 130b, respectively, through the rim of flange portion 134a, 134b.

Treatment head modules 130a, 130b may be received in the hollow portion of shell 118, and the projecting portions 132a, 132b extend through the module track 118a of the shell 118 so that the transducers 136a, 136b protrude from the front of the shell 118 through the module track 118a. (This is shown in the FIG. 4, where the housing portion 112 is shown assembled.) Flange portions 134a, 134b abut the back of the front surface of the shell 118, so the head modules 130a, 130b do not pass through the module track 118a completely. (This is shown in FIG. 7, which includes a cross-sectional view of the apparatus and spine of the patient of FIG. 6.) The module track 118a extends along the length of the oblong shell 118 with a series of transverse broadenings that provide for positioning of head modules 130a, 130b off the center of the length of the shell 118. This allows the ultrasonic transducers to be positioned to the sides of the spinous process 160, so that the ultrasound may be directed toward the vertebral body 162, as shown in FIG. 7.

Referring to FIGS. 4 and 5 together, enclosure 116 is received within the shell 118, and cover 114 and shell 118 are joined together by snap fasteners, such as the series of rigid tabs 118a on shell 118 that interface with the series of slots 114f on cover 114. The enclosure 116 is compressed, because its width is greater than width of shell 118. Consequently, enclosure 118 will press the flange portions 134a, 134b of the head modules 130a, 130b against the back of the front surface of the shell 118, thereby providing a frictional engagement between the enclosure 118, the flange portions 134a, 134b and the shell 118. (FIG. 7 shows flange portions 134a, 134b pressed between the enclosure 116 and the rear portion of the front surface of the shell 118.) This holds the head modules 130a, 130b in a desired position on the module track, with the transducers 136a, 136b protruding from the front of the shell 118 and housing portion 112.

Belt segments 120a, 120b and shoulder straps 113a, 113b are used to engage the housing portion 112 with the spine. Belt segments 120a, 120b attach to each other around the waist of a user by engaging buckle portions 120c, 120d.

Cables 142a, 142b extend from head modules 130a, 130b, respectively, through hole 116a in enclosure 116, as shown in FIG. 5. Plugs 144a, 144b, attach cables 142a, 142b, respectively, into jacks 146a, 146b at the front of cover 114. Wires 148a, 148b extend integrally within cover 114 from jacks 146a, 146b, into external sheathing 150 crossing the interface between cover 114 and belt segment 120a. Wires 148a, 148b continue integrally within belt segment 120a into MOU 140. Thus, when plugs 144a, 144b are received in jacks 146a, 146b, respectively, MOU 140 electrically interfaces with head modules 130a, 130b.

Figure 8:
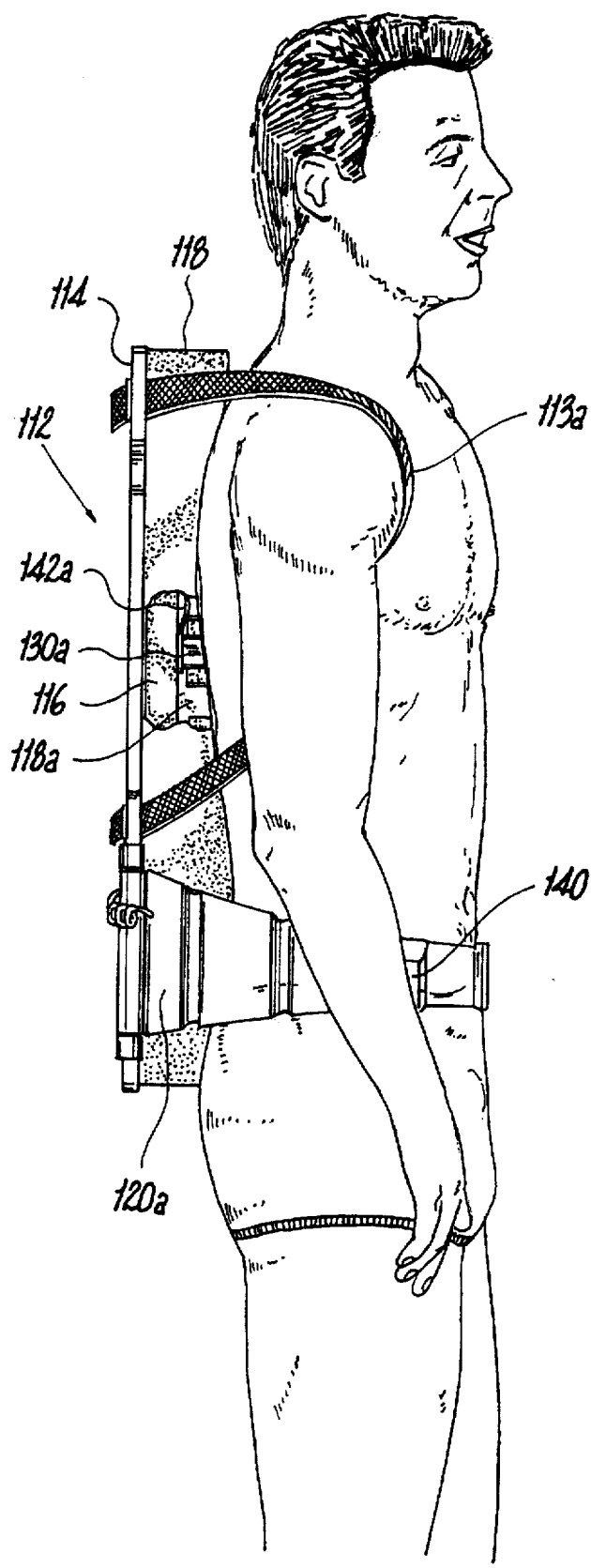
FIG. 8 is a side, partially cut away view of the system of FIGS. 4 and 5 attached for treatment of the lower back and spine of a user.

The design of the spinal treatment apparatus 110 of FIGS. 4–8 allow the use of one or multiple head modules, positioned as required for treatment within the module track &ga. As noted, the contour of the shell 118 is matched with the contour of the spine from the cervical vertebrae to the coccyx. The belt 120a, 120b and the shoulder straps 113a, 113b engage the front of the shell 118 against the patient's back (as shown in FIGS. 6 and 8) so that the treatment heads 130a, 130b deliver treatment to the desired portion of the back. (Although not shown in the figures for this embodiment, conducting gel or other conducting media is interposed between the skin and the transducer surfaces. In particular, an ultrasonic conducting wedge may attach to the front of shell 118, as in the spinal apparatus of FIGS. 1–3.)

Hip Treatment Apparatus

Figure 9:
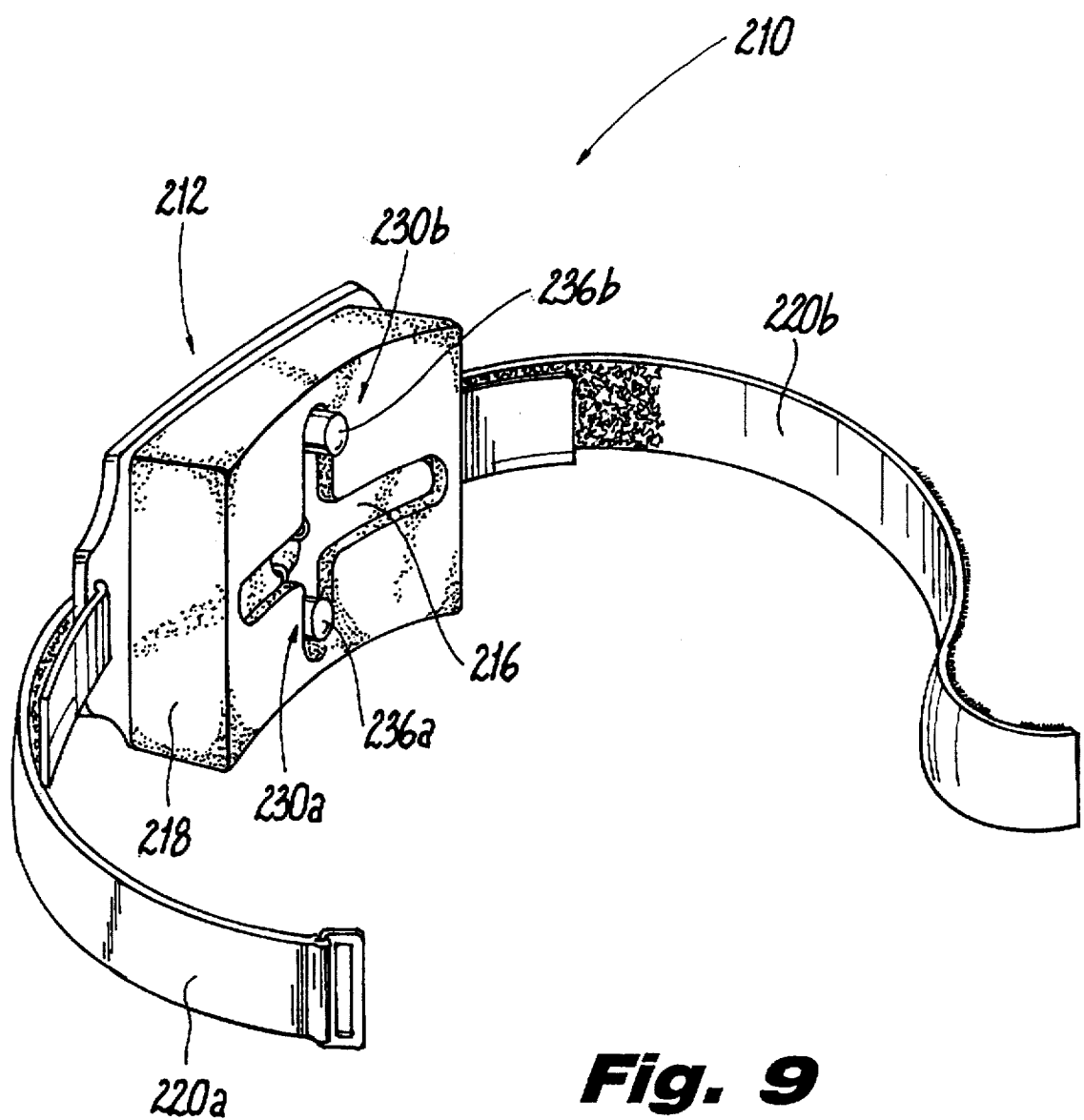
FIG. 9 is a perspective view of a portable module type ultrasonic delivery system configured for use in hip injuries.
Figure 10:
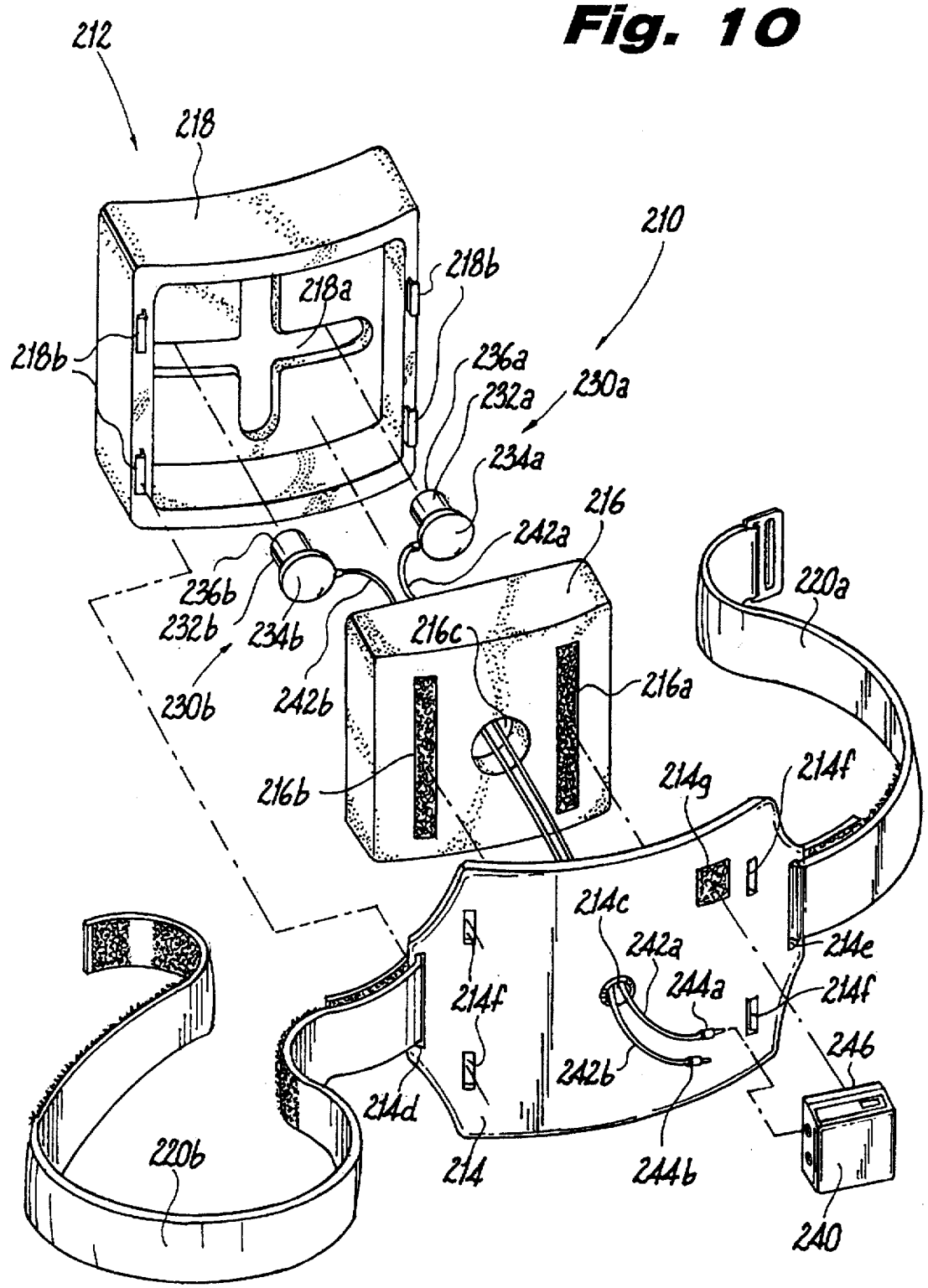
FIG. 10 is an exploded view of the system of FIG. 9, as seen from the opposite direction as in FIG. 9.
Figure 11:
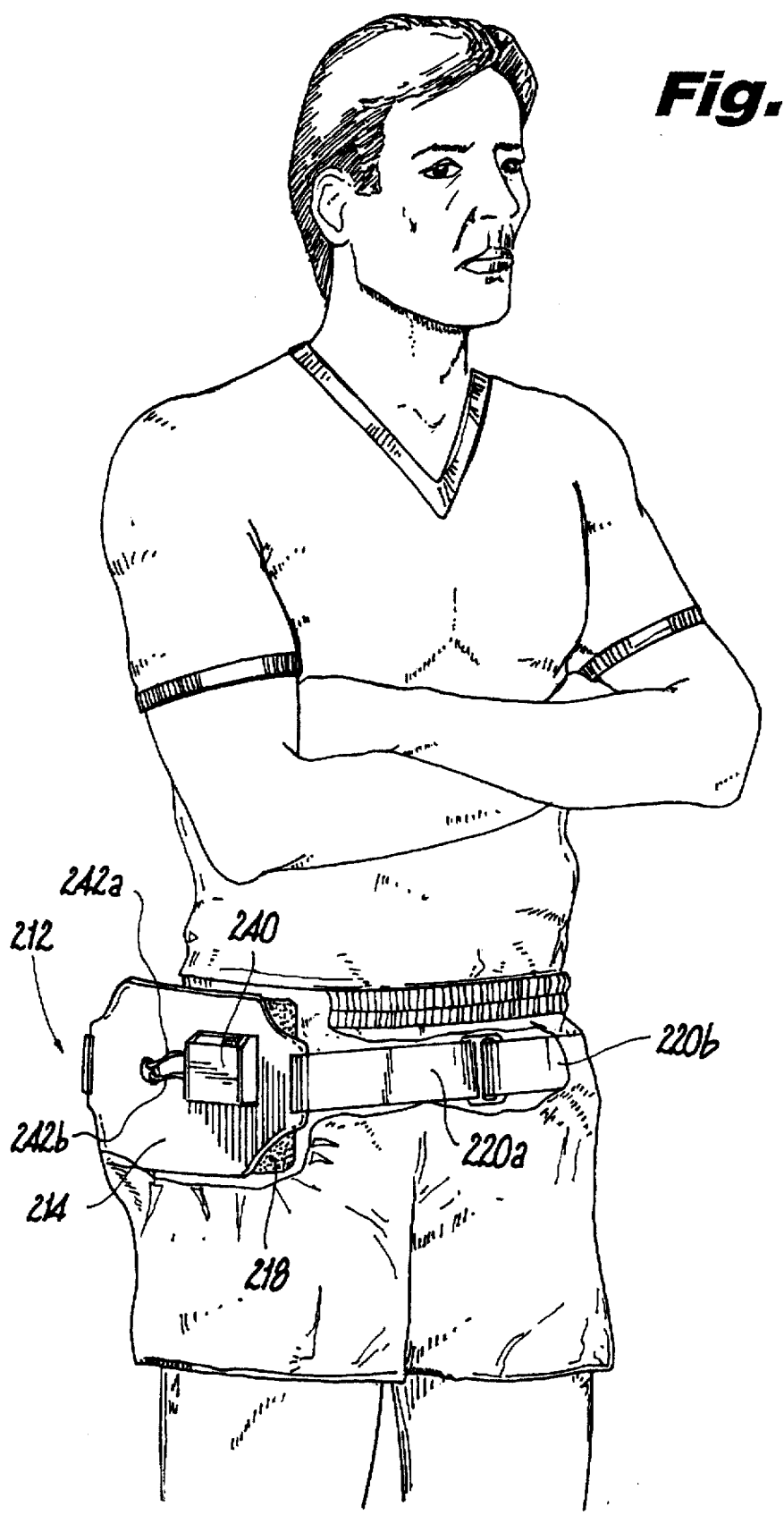
FIG. 11 is a view of the system of FIGS. 9 and 10 attached for treatment of the hip of a user.

FIGS. 9–11 shows a preferred embodiment of an apparatus for delivering ultrasonic therapeutic treatment to the hip. It includes many similar features to the spinal treatment apparatus shown in FIGS. 1–3 and described above. Thus, to facilitate the description of this apparatus, reference will be made to that description (referred to as the "spinal apparatus"), where convenient.

FIG. 9 is a perspective view of the hip treatment apparatus 210, which includes a treatment head module housing portion 212 attached to two belt portions 220a, 220b. Two treatment head modules 230a, 230b are shown extending partially from the housing portion 212. (As with the spinal apparatus, the side of the housing portion 212 from which modules 230a, 230b protrude is referred to as the "front" of the housing portion, and its constituent components, described below.)

FIG. 10 is an exploded view of the hip treatment apparatus 210 of FIG. 9 as viewed from the rear of the housing portion 212. Housing portion 212 is comprised of a cover 214, enclosure 216, and shell 218. Cover 214 is approximately square shaped, with eyelets 214d, 214e for affixing belt portions 220b, 220a, respectively, to the sides of cover 214. Cover 214 has a convex curvature when viewed from the rear. Cover 214 may be made of partially flexible plastic. Hole 214c in the center of cover 214 allows cables 242a, 242b to pass, as described below. Loop fastener segments 216a, 216b on enclosure 216 correspond with matching hook fastener segments (not visible in FIG. 10) on the front of cover 214, to position cover 214 with respect to enclosure 216 when the housing portion 212 is assembled.

Enclosure 216 has a substantially square shape, and hole 216c extends through enclosure 216 to allow cables 242a, 242b to pass, as described below. Enclosure 216 is made of a resilient, deformable material, such as foam rubber.

Shell 218 also has a substantially square shape and is preferably made of flexible plastic. Shell 218 has a convex curvature when viewed from the rear. Module track 218a extends through and along the length of the front surface of shell 218, as with the spinal apparatus. Shell 218 is substantially hollow, similar to the spinal apparatus, so that enclosure 216 may be received therein in the same manner as with the spinal apparatus.

Treatment head modules 230a, 230b are configured as those in the spinal apparatus, with a single projecting portion 232a, 232b, a flange portion 234a, 234b, and a transducer surface 236a, 236b. Cables 242a, 242b extend into the rim of flange portions 234a, 234b, respectively.

Treatment head modules 230a, 230b may be received in the hollow portion of shell 218 and module track 218a in the same manner as the spinal apparatus. Referring to FIGS. 9 and 10 together, the constituent parts of the housing portion 212 assemble together as in the spinal apparatus, and the compression of enclosure 216 holds the head modules 230a, 230b in a desired position on the module track 218a, with the transducer surfaces 236a, 236b protruding from the front of the shell 218.

Cables 242a, 242b extend from head modules 230a, 230b, respectively, through the components of the housing portion 212 as in the spinal apparatus, so that plugs 244a, 244b attach cables 242a, 242b, respectively, to MOU 240.

Belt segments 220a, 220b are used to fasten the housing portion 212 against the hip, as shown in FIG. 11. (The transducer heads must be adjacent bare skin, thus the shorts in FIG. 11 are shown partially cut away. In general, although not shown in the figures for this embodiment, conducting gel or other conducting media is interposed between the skin and the transducer surfaces. In particular, an ultrasonic conducting wedge may attach to the front of shell 218, as in the spinal apparatus of FIGS. 1-3.) Belt segments 220a, 220b are removably attached to the cover 214 with hook and eye fastener segments on belt segments 220a, 220b in the same manner as the spinal apparatus. Belt segments 220a, 220b attach to each other around the waist of a user in the same manner as the spinal apparatus. Because of the broad square shape of the housing portion 212 and the profile of the module track 218a, one or multiple transducers may be positioned against a broad region of the hip. The concave curvature of the components of the housing portion 212 ensures that the transducer surfaces 236a, 236b are positioned flush against the chosen area of the hip. Because the housing unit 212 is within the user's reach, on the hip, MOU 240 is attached to the rear portion of cover 214 with hook and eye fastener segments 214g, 246.

Pelvis/Femur Treatment Apparatus

Figure 12:
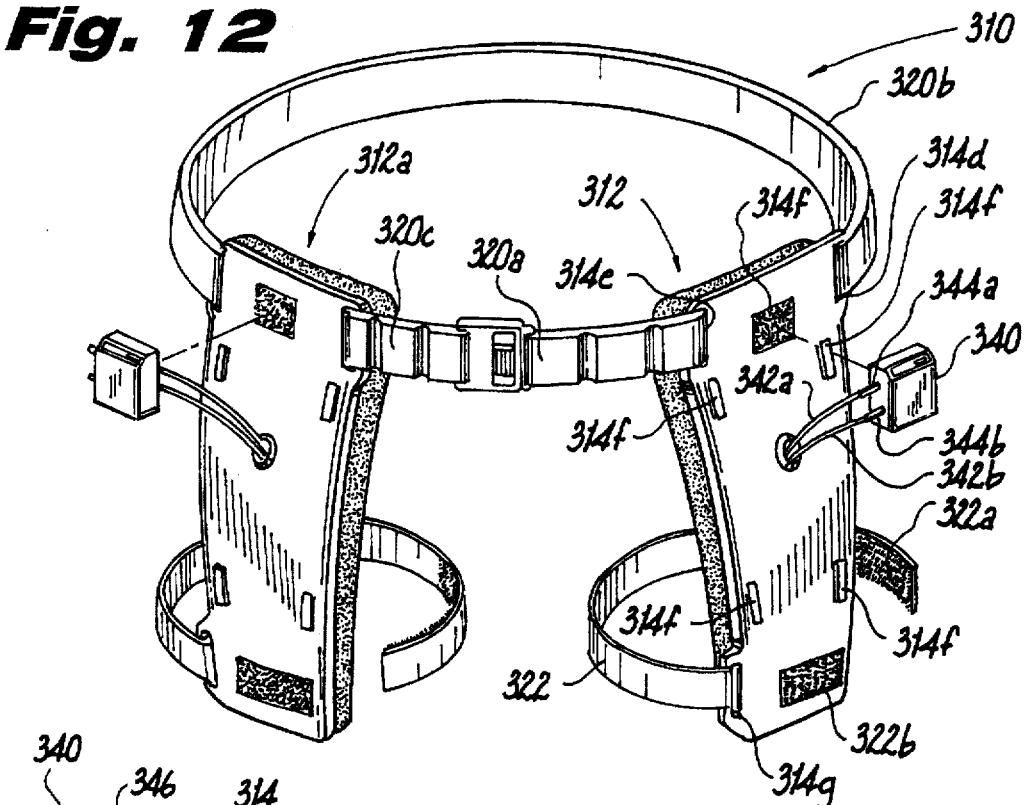
FIG. 12 is a perspective view of a portable module type ultrasonic delivery system configured for use in pelvis and femur injuries.
Figure 13:
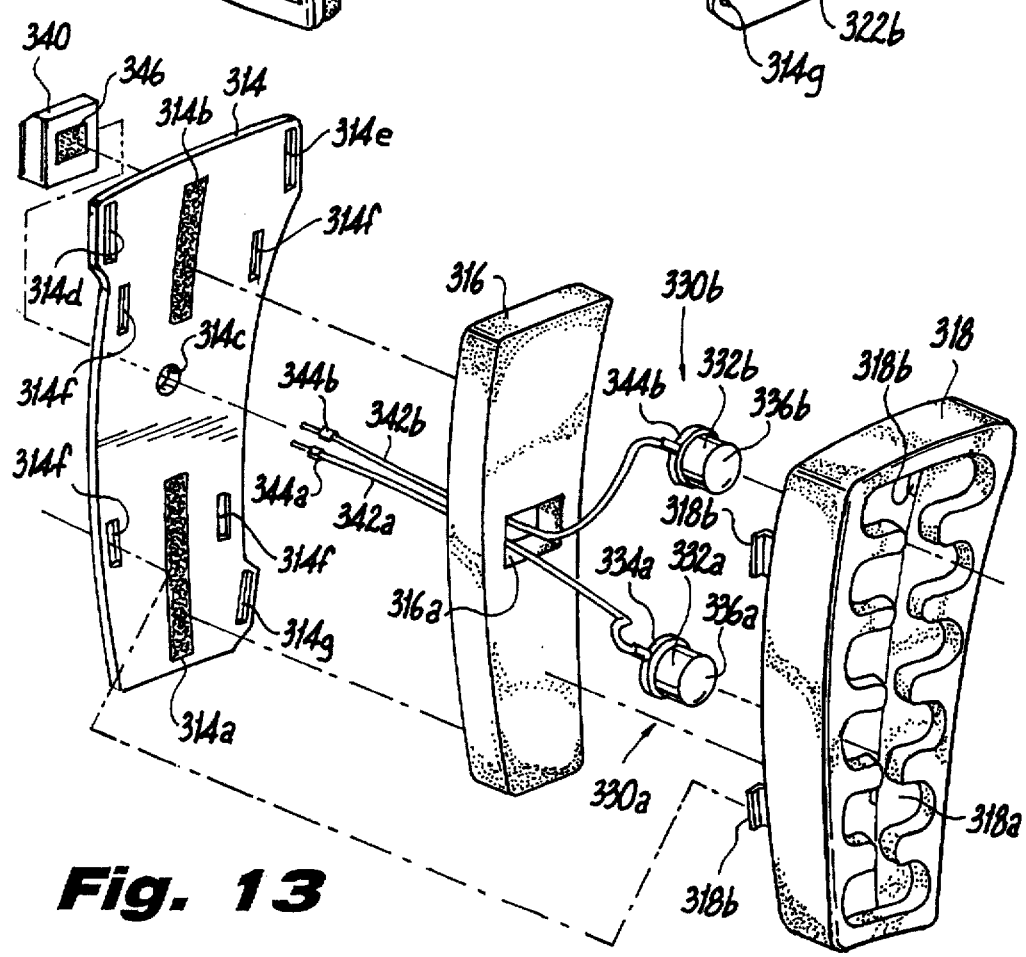
FIG. 13 is an exploded view of the system of FIG. 12, as seen from the opposite direction as in FIG. 12.
Figure 14:
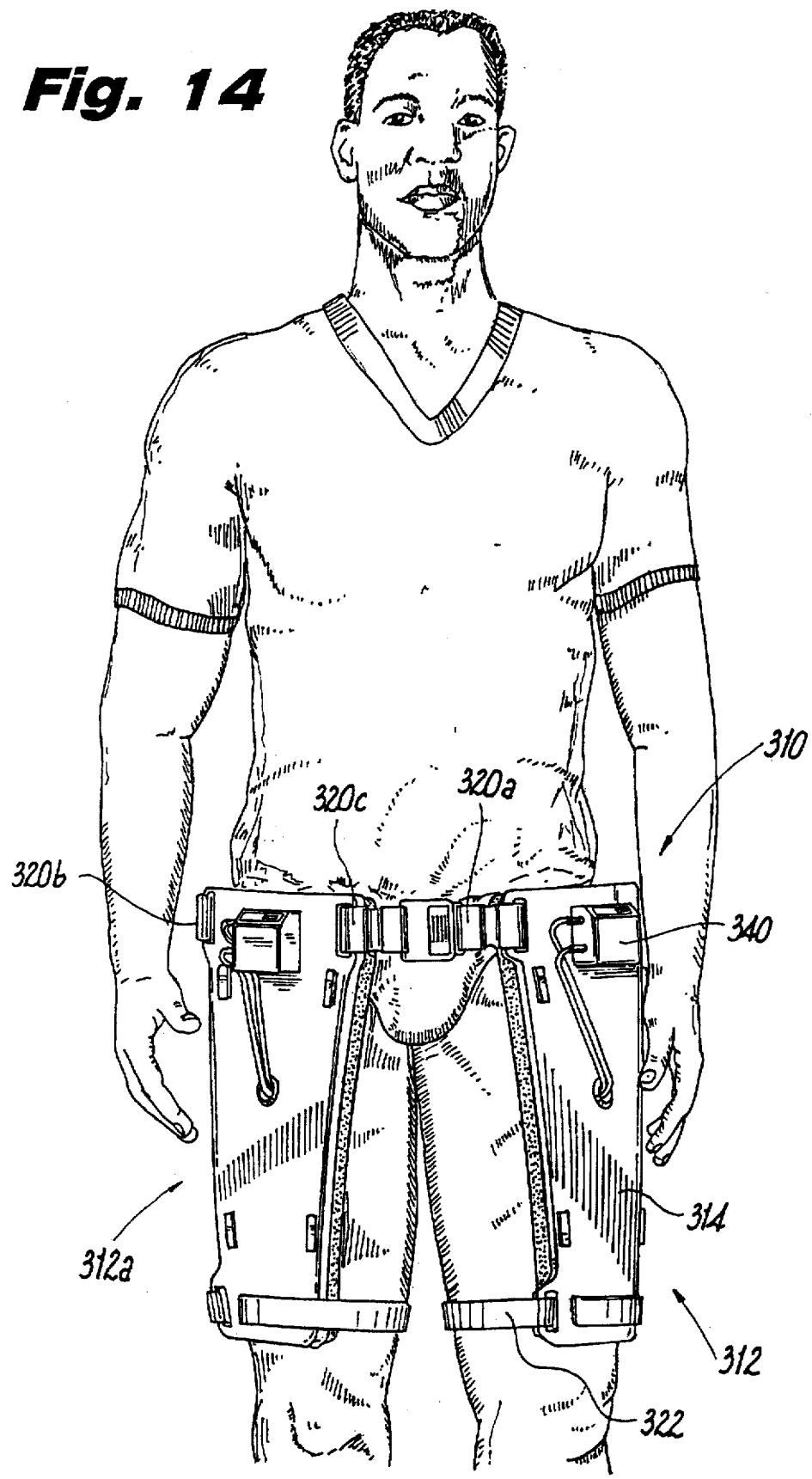
FIG. 14 is a view of the system of FIGS. 12 and 13 attached for treatment of the pelvis and femur of a user.

FIGS. 12-14 show a preferred embodiment of an apparatus for delivering ultrasonic therapeutic treatment to the pelvis and femur. It also includes many features similar to the two spinal treatment apparatus shown in FIGS. 1-3 and described above. Thus, to facilitate the description of this apparatus, reference will again be made to that description of the spinal apparatus, where convenient.

FIG. 12 is a perspective view of the pelvis/femur treatment apparatus 310, which includes a treatment head module housing portion 312 attached to two belt portions 320a, 320b. The belt portions 320a, 320b are attached to cover 314 in the same manner as the spinal apparatus, but through tabbed portions 314d, 314e at the top of tapered, oblong rectangular cover 314, so that the housing portion 312 will be positioned adjacent the pelvis and femur when the belt is fastened about a user's waist. A lower strap 322 interfacing with the housing portion 312 at tabbed portion 314g is used to fasten the housing portion 312 at the femur. (The belt includes a third belt portion 320c. An identical treatment head module housing portion 312a is attached to belt portions 320b, 320c. As shown in FIG. 14 and described below, using two treatment head module housing portions 312, 312a allows both pelvis/femur regions to be treated simultaneously. The description below will focus on housing portion 312, but the other housing portion 312a is identical.)

FIG. 13 is an exploded perspective view of the housing portion 312 of the pelvis treatment apparatus 310 of FIG. 12 as viewed from the side of the housing portion 312 opposite that shown in FIG. 12. (As with the apparatus previously described, FIG. 13 is defined as showing the "front" of the housing portion 312. The direction "up" is with respect to the orientation of the housing portion 312 in FIG. 13.) Housing portion 312 is comprised of a cover 314, enclosure 316, and shell 318. Cover 314 is approximately rectangularly shaped and tapers together from the top of the device to the bottom, where it engages the femur region (as shown in FIG. 14 and described below). Tabbed portions 314d, 314e adjacent the top of the cover 314 receive belt portions 320a, 320b and tabbed portion 314g receives strap 322. Cover 314 may be made of partially flexible plastic. Cover 314 has a concave curvature when viewed from the front. Hole 314c in the center of cover 314 allows cables 342a, 342b to pass, as described below. Strips of hook fasteners 314a, 314b on cover 314 correspond with matching strips of loop fasteners (not visible in FIG. 13) on enclosure 316, and position cover 314 with respect to enclosure 316 when the housing portion 312 is assembled.

Enclosure 316 is rectangularly shaped and tapers together towards the bottom, as does cover 314. Hole 316a extends through enclosure 316 to allow cables 342a, 342b to pass, as described below. Enclosure 316 may be made of a resilient, deformable material, such as foam rubber.

Shell 318 also has a rectangular shape and tapers together towards the bottom, as does cover 314, and is preferably made of flexible plastic. Shell 318 has a concave curvature when viewed from the front. Module track 318a extends through and along the length of the front surface of shell 318, as in the spinal apparatus. Shell 318 is substantially hollow, similar to the spinal apparatus, so that enclosure 316 may be received therein in the same manner as with the spinal apparatus.

Treatment head modules 330a, 330b are configured as those in the spinal apparatus, with a single projecting portion 332a, 332b, a flange portion 334a, 334b, and a transducer surface 336a, 336b. Cables 342a, 342b extend into rims of flange portions 334a, 334b, respectively.

Treatment head modules 330a, 330b may be received in the hollow portion of shell 318 and module track 318a in the same manner as the spinal apparatus. Referring to FIGS. 12 and 13 together, the constituent parts of the housing portion 312 assemble together as in the spinal apparatus, and the compression of enclosure 316 holds the head modules 330a, 330b in a desired position on the module track, with the transducers 336a, 336b protruding from the front of the shell 318.

Cables 342a, 342b extend from head modules 330a, 330b, respectively, through the components of the housing portion 312 as in the spinal apparatus, so that plugs 344a, 344b attach cables 342a, 342b, respectively, to MOU 340.

Referring to FIGS. 12 and 14, belt segments 320a, 320b, 320c surrounds the waist of the user and are used to fasten the housing portion 312 against the pelvis and femur. Strap 322 surrounds the thigh of the user (via hook and loop fastener segments 322a, 322b) to fasten the lower portion of the housing portion 312 against the femur. Because of the oblong rectangular shape of the housing portion 312 and the extensive profile of the module track 318a, one or multiple transducers may be placed against a broad region of the pelvis and/or the femur. The concave curvature of the components of the housing portion 312 ensures that the transducers 336a, 336b are positioned adjacent the skin area corresponding to the pelvis and/or the femur when the belt 320a, 320b, 320c is attached around the user's waist, as shown in FIG. 14. (In general, although not shown in the figures for this embodiment, conducting gel or other conducting media is interposed between the skin and the transducer surfaces. In particular, an ultrasonic conducting wedge may attach to the front of shell 318, as in the spinal apparatus of FIGS. 1–3.) As also seen in FIG. 14, MOU 340 is attached to the rear portion of cover 314, so that it is within the user's reach during treatment of the pelvis. (Again, FIGS. 12 and 14 show an identical housing portion 328a that corresponds to the patient's other pelvis and femur region. Thus, the apparatus 310 may be used to treat both pelvis and femur regions simultaneously.)

Clavicle Treatment Apparatus

Figure 15:
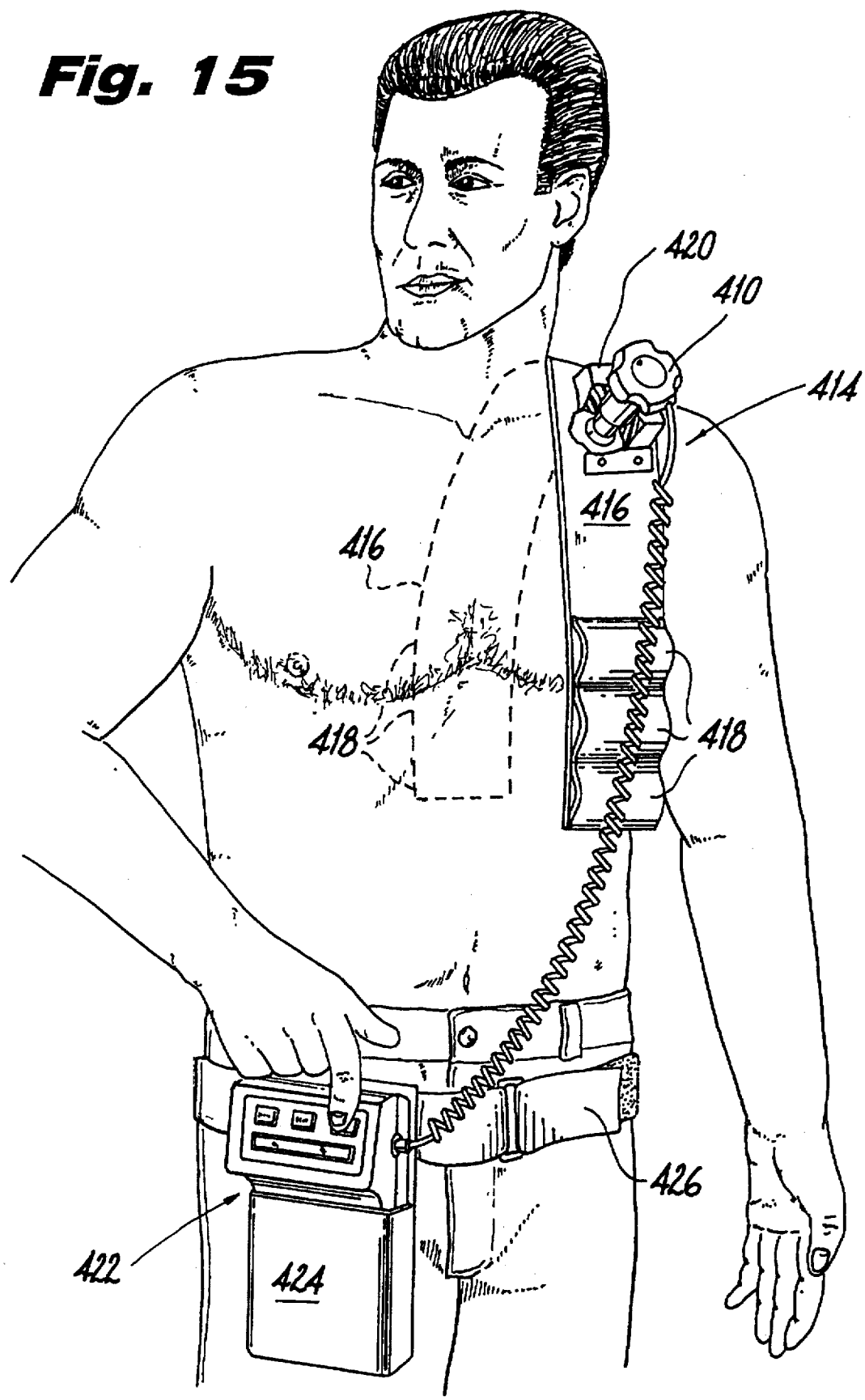
FIG. 15 is a perspective, partially cut-away view of a portable module type ultrasonic delivery system configured for use in clavicle injuries.

Referring to FIG. 15, a preferred embodiment of the present invention is shown in application to a patient with an injury of the torso, in this case, a clavicle injury. Clavicle injuries present a particularly difficult problem in efficiently applying ultrasound to the site adjacent the injury. This is caused by the uneven topography of the skin and musculoskeletal structure in the clavicle region and the difficulty in maintaining the operative surface of the treatment head module 410 in the necessary orientation for effective treatment. For a clavicle injury, the treatment head module 410 is held in position by a harness 414 including a draped belt 416 with weighted inserts 418 and a mounting portion 420. (The mounting portion 420 completely surrounds the head module 410, however, in FIG. 15 it is shown partially cut away to show the head module 410 inserted therein.) Belt 416 is draped over the chest and back of the patient with the treatment head module 410 (and, preferably, a gel bladder covering the transducer surface of the head module 410) positioned operatively adjacent the site of the injury on the clavicle. The weighted inserts 418 of the belt 416 maintain the transducer housing in a uniform position for treatment, while the MOU 422 is attached to the user's waist by a pouch 424 mounted on a hip belt 426.

Figure 16:
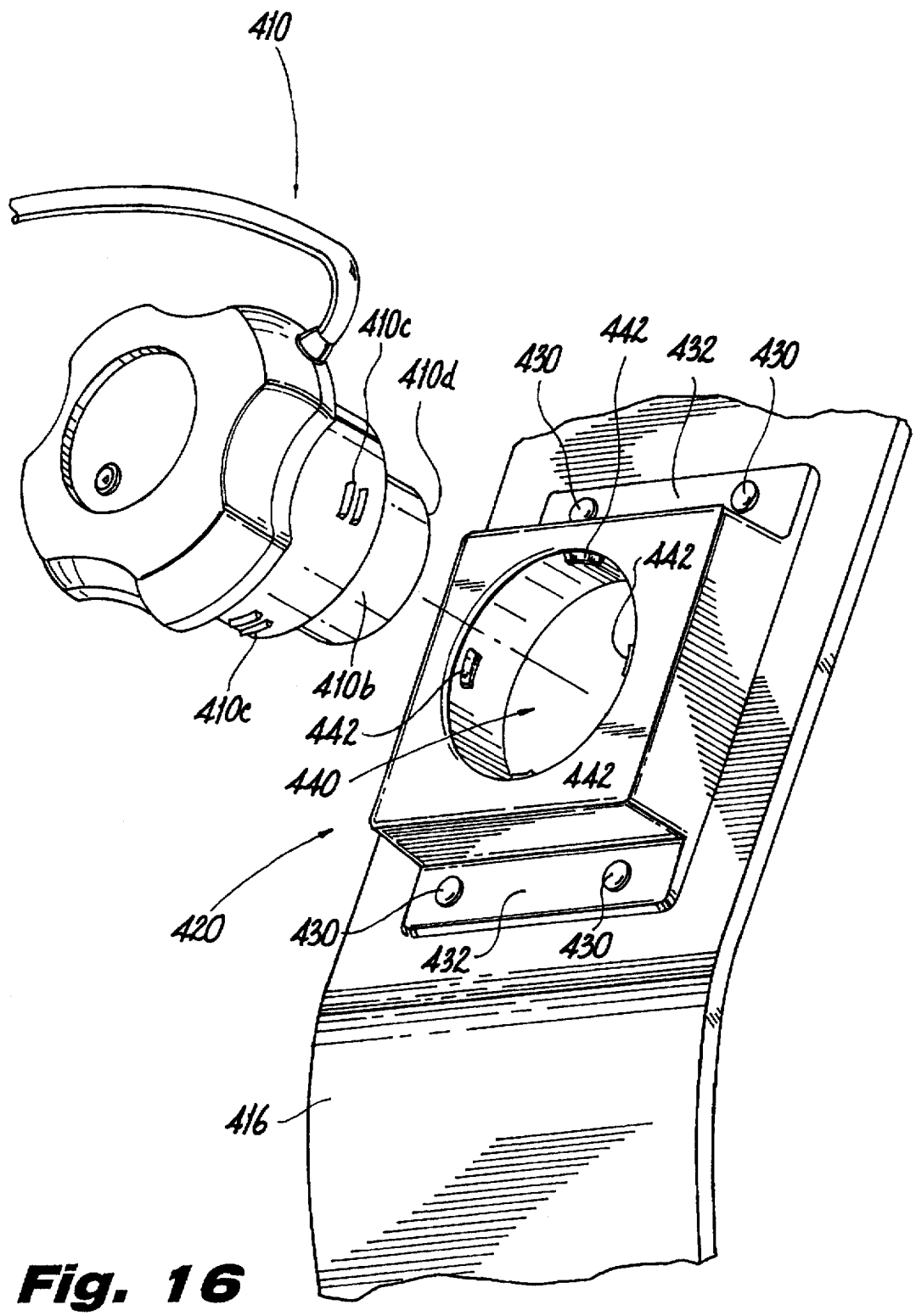
FIG. 16 is a more detailed perspective view of components of the ultrasonic delivery system of FIG. 15.

FIG. 16 shows the mounting portion 420 on the belt 416, with the treatment head module 410 disengaged. Mounting portion 420 is affixed to the belt 416 by rivets 430 through flanged portions 432. The mounting portion 420 also has a circular aperture 440 and bayonet locking lugs 442.

Head module 410 has first module projection 410a of diameter greater than second module projection 410b, both of which are received in aperture 440 of mounting portion 420. (Head module 410 as shown in FIGS. 15 and 16 house treatment head module electronic circuitry such as that in U.S. patent application Ser. No. 08/389,148, incorporated by reference above. The surface of transducer 410d is adjacent the exposed face of second module projection 410b.) Aperture 440 has a slightly larger diameter than first module projection 410a of head module 410. This provides space for slotted lugs 410c on the first module projection 410a to also be received in aperture 440. Likewise, bayonet lugs 442 extending from mounting portion 420 into aperture 440 do not impede reception of first module projection 410a in aperture 440.

Second and first module projections 410a, 410b of head module 410 are inserted into aperture 440 with slotted lugs 410c offset from bayonet lugs 442. The transducer surface 410d is pressed adjacent the skin location adjacent the clavicle and the transducer treatment head module 410 is then rotated with respect to the mounting portion 420 so that the slotted lugs 410c engage the bayonet lugs 442. Ultrasonic treatment of the clavicle then commences. (Although not shown for this particular embodiment, in general, conducting gel or other conducting media is interposed between the skin and the transducer surface.)

Preferably, for all of the above applications, the operative surface or transducer surface of the transducer treatment head module includes a gel sensing element for confirming the presence of ultrasonic conductive material adjacent the transducer or operative surface.

It will be understood that various modifications can be made to the various embodiments of the present invention herein disclosed without departing from its spirit and scope. For example, various shapes of the different housing portions that engage the above-described, or other regions of the torso, are contemplated, as well as various types of construction materials. Therefore the above description should not be construed as limiting the invention but merely as presenting preferred embodiments of the invention. Those skilled in the art will envision other modifications within the scope and spirit of the present invention as defined by the claims presented below.

What is claimed is:

1. Ultrasonic delivery system for therapeutic use having:
    a main operating unit, including a signal generator for providing excitation signals for an ultrasonic transducer head module;
    at least one ultrasonic treatment head module, the head module including a receiving component and an ultrasonic generation component for providing ultrasonic waves from an exposed operative surface positionable adjacent a skin location, the receiving component receiving the excitation signals from the signal generator and providing input signals to the ultrasonic generation component for the generation of ultrasonic waves at the operative surface;
    an interface between the main operating unit and the receiving component of the ultrasonic treatment head module for transmitting the excitation signals from the signal generator to the receiving component; and
    an attachment including a housing portion configured to the contour of a region of the human torso and that houses the at least one treatment head module, the housing portion having a module track from which the operative surface of the at least one treatment head module protrudes to the exterior of the housing portion, the module track being configured to slidably receive the at least one treatment head module to permit movement of the at least one treatment head module to different skin locations.

2. Ultrasonic delivery system as in claim 1, wherein the attachment is configured to contour at least in part to the clavicle region of the torso of a human body.

3. Ultrasonic delivery system as in claim 1, wherein the attachment is comprised of a housing portion that is configured to the contour of a region of the human torso and that houses at least one treatment head module, the housing portion having a module track in a side thereof, from which the operative surface of the at least one treatment head module protrudes to the exterior of the housing portion, and an adjustable belt that interfaces with the housing portion and surrounds a portion of the torso, so that the housing portion is adjacent the region of the torso it is contoured to, and the operative surface of the at least one ultrasonic head module is adjacent a skin location on the torso.

4. Ultrasonic delivery system as in claim 3, wherein the housing portion is configured to contour at least in part to the spinal region of the torso of a human body.

5. Ultrasonic delivery system as in claim 3, wherein the housing portion is configured to contour at least in part to the hip region of the torso of a human body.

6. Ultrasonic delivery system as in claim 3, wherein the housing portion is configured to contour at least in part to the pelvis region of the torso of a human body.

7. Ultrasonic delivery system as in claim 6, wherein the housing portion is additionally configured to contour at least in part to the femur region of a human body.

8. Ultrasonic delivery system as in claim 3, wherein a conducting media wedge attaches to the housing portion, so that conducting media is interposed between the operative surface of the at least one ultrasonic head module and the adjacent external skin location on the torso.

9. Ultrasonic delivery system as in claim 3, wherein the at least one ultrasonic treatment head module is positionable at variable locations within the module track.

10. Ultrasonic delivery system as in claim 1, wherein the attachment is a housing portion with at least one ultrasonic treatment head module at least partially enveloped therein, the operative surface protruding from a surface of the housing portion, and an adjustable belt that may surround the torso and interface with the housing portion such that the operative surface of the at least one ultrasonic head module is adjacent a skin location on the torso.

11. Ultrasonic delivery system as in claim 10, wherein the housing portion is configured to contour at least in part to the spinal region of the torso of a human body.

12. Ultrasonic delivery system as in claim 10, wherein the housing portion is configured to contour at least in part to the hip region of the torso of a human body.

13. Ultrasonic delivery system as in claim 10, wherein the housing portion is configured to contour at least in part to the pelvis region of the torso of a human body.

14. Ultrasonic delivery system as in claim 13, wherein the housing portion is additionally configured to contour at least in part to the femur region of a human body.

15. Ultrasonic delivery system as in claim 10, wherein a conducting media wedge attaches to the housing portion, so that conducting media is interposed between the operative surface of the at least one ultrasonic head module and the adjacent external skin location on the torso.

16. Ultrasonic delivery system as in claim 1, wherein the main operating unit is positioned within a pouch worn by the patient to permit portable operation thereof.

17. Ultrasonic delivery system as in claim 1, wherein the main operating unit is attached to the attachment.

18. Ultrasonic delivery system as in claim 1, wherein the ultrasonic treatment head module has a telescoping portion defining a forward planar region, the exposed operative surface substantially parallel with the forward planar region.

19. Ultrasonic delivery system as in claim 18, wherein the receptacle means includes an aperture to receive the telescoping portion of the ultrasonic treatment head module.

20. Ultrasonic delivery system as in claim 19, wherein the receptacle means has at least two bayonet lugs extending into the aperture.

21. Ultrasonic delivery system as in claim 20, wherein the telescoping portion of the ultrasonic treatment head module includes at least two slotted lugs engagable with the at least two bayonet lugs on the receptacle portion.

22. Ultrasonic delivery system for therapeutic use having:
a main operating unit, including a signal generator for providing excitation signals for an ultrasonic transducer head module;
at least one ultrasonic treatment head module, the head module including a receiving component and an ultrasonic generation component for providing ultrasonic waves from an exposed operative surface positionable adjacent a skin location, the receiving component receiving the excitation signals from the signal generator and providing input signals to the ultrasonic generation component for the generation of ultrasonic waves at the operative surface;
an interface between the main operating unit and the receiving component of the ultrasonic treatment head module for transmitting he excitation signals from the signal generator to the receiving component; and
an attachment configured to contour at least in part to a region of the torso of a human body, the attachment including receptacle means adapted for holding the at least one ultrasonic treatment head module with the operative surface adjacent a skin location in the torso region when the attachment is positioned adjacent the torso region it is contoured to,
wherein the attachment is configured to contour at least in part to the clavicle region of the torso of a human body and includes a flexible strap having weighted end portions, the receptacle means positioned in an intermediate portion of the strap, so that the strap may be draped over the shoulder with the receptacle positioned adjacent the clavicle region.

23. Ultrasonic delivery system for therapeutic use having
at least one ultrasonic treatment module with a telescoping portion, the distal end of the telescoping portion defining a forward planar region;
ultrasonic generation means housed within the at least one ultrasonic treatment module and including an exposed operative surface substantially parallel with the forward planar region of the telescoping portion;
a positionable receptacle for retaining and aligning the at least one ultrasonic treatment module with the operative surface adjacent a skin location on a region on the torso of a human body the receptacle being configured to receive a plurality of the ultrasonic treatment modules.

24. Ultrasonic delivery system as in claim 23, wherein the receptacle is a housing portion that at least in part envelops the at least one ultrasonic treatment head module with the operative surface exposed and positionable adjacent a skin location.

25. Ultrasonic delivery system as in claim 24, wherein the housing portion is configured to contour at least in part to the spinal region of the torso of a human body.

26. Ultrasonic delivery system as in claim 24, wherein the housing portion is configured to contour at least in part to the hip region of the torso of a human body.

27. Ultrasonic delivery system as in claim 24, wherein the housing portion is configured to contour at least in part to the pelvis region of the torso of a human body.

28. Ultrasonic delivery system as in claim 27, wherein the housing portion is additionally configured to contour at least in part to the femur region of the human body.

29. Ultrasonic delivery system as in claim 24, wherein a conducting media wedge attaches to the housing portion, so that conducting media is interposed between the operative surface and the adjacent skin location.

30. Ultrasonic delivery system as in claim 24, further comprising an adjustable belt that may surround the torso and interface with the housing portion, whereby the at least one ultrasonic treatment head module engages a skin location on the torso.

31. Ultrasonic delivery system for therapeutic use having at least one ultrasonic treatment module with a telescoping portion, the distal end of the telescoping portion defining a forward planar region;

ultrasonic generation means housed within the at least one ultrasonic treatment module and including an exposed operative surface substantially parallel with the forward planar region of the telescoping portion;

a positionable receptacle for remaining and aligning the at least one ultrasonic treatment module with the operative surface adjacent a skin location on a region on the torso of a human body wherein the positionable receptacle is comprised of at least one mounting portion attached to a flexible strap having weighted end portions, the mounting portion attached at an intermediate portion of the strap, so that the strap may be draped over the shoulder with the mounting portion located adjacent the clavicle region.

* * * * *